US00PP12158P2

(12) United States Plant Patent
Fuess

(10) Patent No.: US PP12,158 P2
(45) Date of Patent: Oct. 23, 2001

(54) CHRYSANTHEMUM PLANT NAMED 'EMPIRE PIZZAZZ'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/475,974

(22) Filed: Dec. 31, 1999

(51) Int. Cl.[7] ..... A01H 5/00

(52) U.S. Cl. ..... Plt./293

(58) Field of Search ..... Plt./287, 293

(56) References Cited

U.S. PATENT DOCUMENTS

P.P. 6,938 * 7/1989 VandenBerg ..... Plt./293

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Empire Pizzazz', characterized by its outwardly spreading and freely branching habit; decorative-type inflorescences that are about 4.5 to 5.5 cm in diameter; numerous attractive bright red ray florets; ray floret color that resists fading with development; compact cushion habit; numerous inflorescences per plant; early flowering response; and excellent garden performance.

1 Drawing Sheet

BACKGROUND OF THE INVENTION

The present invention relates to a new and distinct cultivar of Chrysanthemum plant, botanically known as *Dendranthema grandiflora* and hereafter referred to by the cultivar name Empire Pizzazz.

The new cultivar is a product of a planned breeding program conducted by the Inventor in New Hartford, N.Y. The objective of the breeding program is to create new garden-type Chrysanthemum cultivars having inflorescences with desirable inflorescence forms, attractive floret colors and good garden performance.

The new cultivar originated from a cross made by the Inventor in 1996, of the *Dendranthema grandiflora* cultivar Empire Diablo, disclosed in U.S. Plant Pat. No. 9,586, as the female, or seed parent, with a proprietary seedling selection identified as H87-23 as the male, or pollen parent, described as a dark red decorative-type garden Chrysanthemum.

The cultivar Empire Pizzazz was discovered and selected by the Inventor as a flowering plant within the progeny of the stated cross in a controlled environment in New Hartford, N.Y., in September, 1997. The selection of this plant was based on its desirable inflorescence form, attractive ray floret color and excellent garden performance.

Asexual reproduction of the new cultivar by terminal cuttings taken in a controlled environment in New Hartford has shown that the unique features of this new Chrysanthemum are stable and reproduced true to type in successive generations.

BRIEF SUMMARY OF THE INVENTION

The cultivar Empire Pizzazz has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Pizzazz'. These characteristics in combination distinguish 'Empire Pizzazz' as a new and distinct cultivar:

1. Outwardly spreading and freely branching habit.
2. Decorative-type inflorescences that are about 4.5 to 5.5 cm in diameter.
3. Numerous attractive bright red ray florets; color resists fading with development.
4. Compact cushion habit.
5. Numerous inflorescences per plant.
6. Early flowering response.
7. Excellent garden performance.

Plants of the new Chrysanthemum flower slightly later than plants of the female parent, the cultivar Empire Diablo, under artificially-manipulated daylengths. In addition, plants of the new Chrysanthemum have lighter red ray florets and slightly smaller inflorescences than plants of the cultivar Empire Diablo.

BRIEF DESCRIPTION OF THE PHOTOGRAPH

The accompanying photograph illustrates the overall appearance of the new cultivar as true as it is reasonably possible to obtain in colored reproductions of this type. Colors in the photograph may differ slightly from the color values cited in the detailed botanical description which more accurately describe the actual colors of the new Chrysanthemum. The photograph comprises a top perspective view of a typical flowering plant of 'Empire Pizzazz'.

DETAILED BOTANICAL DESCRIPTION

In the following description, color references are made to The Royal Horticultural Society Colour Chart except where general terms of ordinary dictionary significance are used. The following observations and measurements describe plants grown in 20-cm containers in New Hartford under outdoor natural season conditions which approximate those generally used in commercial garden Chrysanthemum production. Measurements and comparisons were determined on Sep. 15, 1999 about mid-day under 4,000 foot-candles of light in New Hartford, N.Y.

Botanical classification: *Dendranthema grandiflora* cultivar Empire Pizzazz.

Commercial classification: Decorative-type garden chrysanthemum.

Parentage:

*Female or seed parent.*—*Dendranthema grandiflora* cultivar Empire Diablo, disclosed in U.S. Plant Pat. No. 9,586.

*Male or pollen parent.*—Proprietary seedling selection identified as H87-23; a dark red decorative-type garden Chrysanthemum.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Outwardly spreading and mounding. Freely branching.

*Plant height.*—About 25 to 30 cm.

*Foliage description.*—Leaf arrangement: Alternate. Length: About 6 to 7 cm. Width: About 3.5 to 4 cm. Base: Attenuate. Margin: Five-lobed. Color: Mature foliage upper surface: 147A. Mature foliage lower surface: 147B.

Inflorescence description:

*Appearance.*—Decorative-type inflorescence form; almost fully double inflorescences with few disc florets. Compact cushion habit. Inflorescences borne on terminals above foliage, arising from leaf axils. Ray florets arranged acropetally on a capitulum. One inflorescence per terminal with numerous inflorescences per plant.

*Flowering response.*—Under natural conditions, plants flower about September 16th in New Hartford, N.Y. Plants exposed to artificially-manipulated day-lengths will flower about 7.5 weeks after start of long nyctoperiod treatments.

*Inflorescence diameter.*—About 4.5 to 5.5 cm.

*Ray florets.*—Length: About 2.25 cm. Width: About 5 mm. Number of ray florets per inflorescence: About 195 to 205. Color, opened inflorescence: Upper surface: Bright red, 179A; color resists fading with subsequent development. Lower surface: 179C.

*Disc florets.*—Shape: Tubular, apex dentate. Number of disc florets per inflorescence: About 22. Color: Immature: 5A. Mature: 7A.

*Reproductive organs.*—Androecium: Present on disc florets only. Pollen: Scarce. Gynoecium: Present on both ray and disc florets. Style appearance: Bifurcate; enclosed in anther ring on disc florets. Style length: Ray florets, about 5 mm; disc florets, about 3 mm.

*Seed.*—Seed production has not been observed.

Disease resistance: Resistance to known Chrysanthemum diseases has not been observed on plants grown under commercial production conditions.

It is claimed:

1. A new and distinct cultivar of Chrysanthemum plant named 'Empire Pizzazz', as illustrated and described.

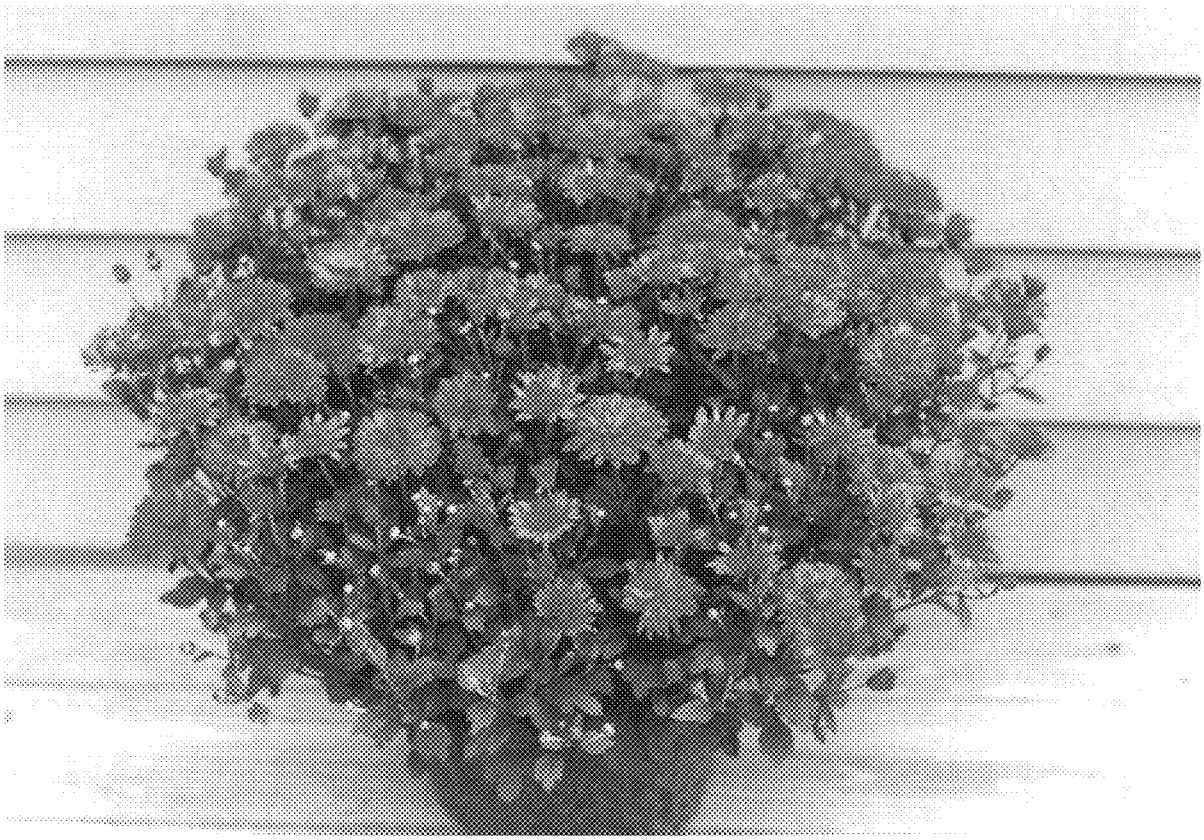

* * * * *